United States Patent
Shim et al.

(10) Patent No.: US 6,508,103 B1
(45) Date of Patent: Jan. 21, 2003

(54) IMPACT DROP TESTER FOR PORTABLE CONSUMER PRODUCTS

(75) Inventors: Victor Phyau Wui Shim, Singapore (SG); Chwee Teck Lim, Singapore (SG)

(73) Assignee: National University of Singapore (SG)

( * ) Notice: Subject to any disclaimer, the term of this patent is extended or adjusted under 35 U.S.C. 154(b) by 0 days.

(21) Appl. No.: 09/592,262

(22) Filed: Jun. 13, 2000

(30) Foreign Application Priority Data

Jun. 14, 1999 (SG) .......................................... 9902933-2

(51) Int. Cl.⁷ ............................................. G01N 19/02
(52) U.S. Cl. ..................................... 73/12.06; 73/12.09
(58) Field of Search ............................ 73/12.06, 12.09, 73/12.13, 12, 12.04, 12.14

(56) References Cited

U.S. PATENT DOCUMENTS

| | | | |
|---|---|---|---|
| 3,412,598 A | | 11/1968 | Nebb |
| 3,426,578 A | | 2/1969 | Berg |
| 4,069,704 A | * | 1/1978 | Grant, Jr. et al. ................ 73/38 |
| 4,363,649 A | * | 12/1982 | Yamato et al. ................ 65/158 |
| 4,531,401 A | * | 7/1985 | Nelson et al. ............. 73/12.02 |
| 4,910,995 A | | 3/1990 | Nishio ....................... 73/12.06 |
| 5,390,535 A | * | 2/1995 | Smock et al. .................. 73/79 |
| 5,431,060 A | * | 7/1995 | Laren .......................... 73/831 |
| 5,696,312 A | * | 12/1997 | Lee et al. .................. 73/12.13 |
| 5,739,411 A | * | 4/1998 | Lee et al. .................. 73/12.13 |
| 5,824,880 A | * | 10/1998 | Burwell et al. ............ 73/12.06 |

FOREIGN PATENT DOCUMENTS

| | | |
|---|---|---|
| GB | 2 217 024 | 10/1989 |
| JP | A1239465 | 9/1989 |
| JP | 09-318484 | 12/1997 |

* cited by examiner

*Primary Examiner*—Benjamin R. Fuller
*Assistant Examiner*—Andre Allen
(74) *Attorney, Agent, or Firm*—Birch, Stewart, Kolasch & Birch, LLP

(57) ABSTRACT

A drop tester (1) including a gripper mechanism (2) for holding a product (37) to be tested, a guide track, a slider block (3) which is mounted to slide along the guide track and advance the mechanism toward a target location (41) and a release device (40) for triggering release of the product from the mechanism to impact at the target location, characterised in that the gripper mechanism includes gripper arms (15, 16) coupled to the slider block, the gripper arms being rotatable relative to the slider block to enable the orientation of the product to be varied, relative to the target location. The slider block is preferably releasably coupled to a hoisting block (4) which is positionable at a predetermined location along the guide track. More preferably, the gripper arms are pivotally mounted to a housing (23) and coupled to a piston (22) provided within the housing, the arms pivoting between a gripping position and a release position upon advancement of the piston through the housing.

15 Claims, 4 Drawing Sheets

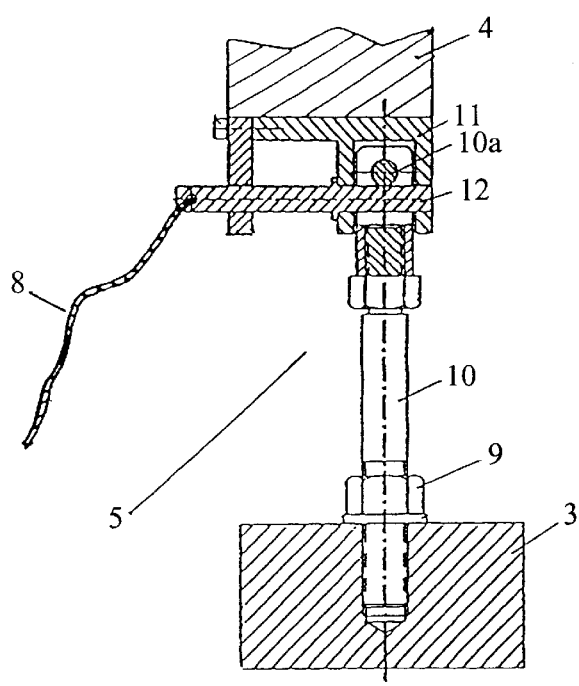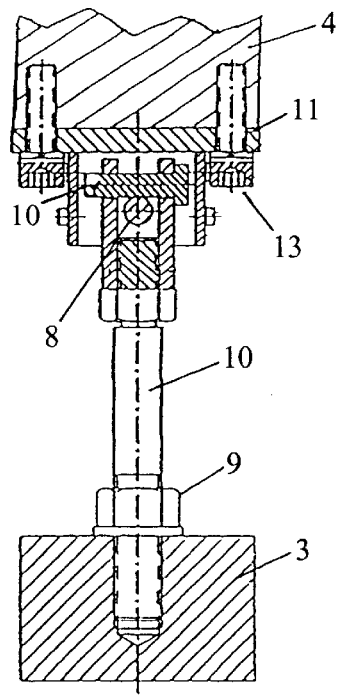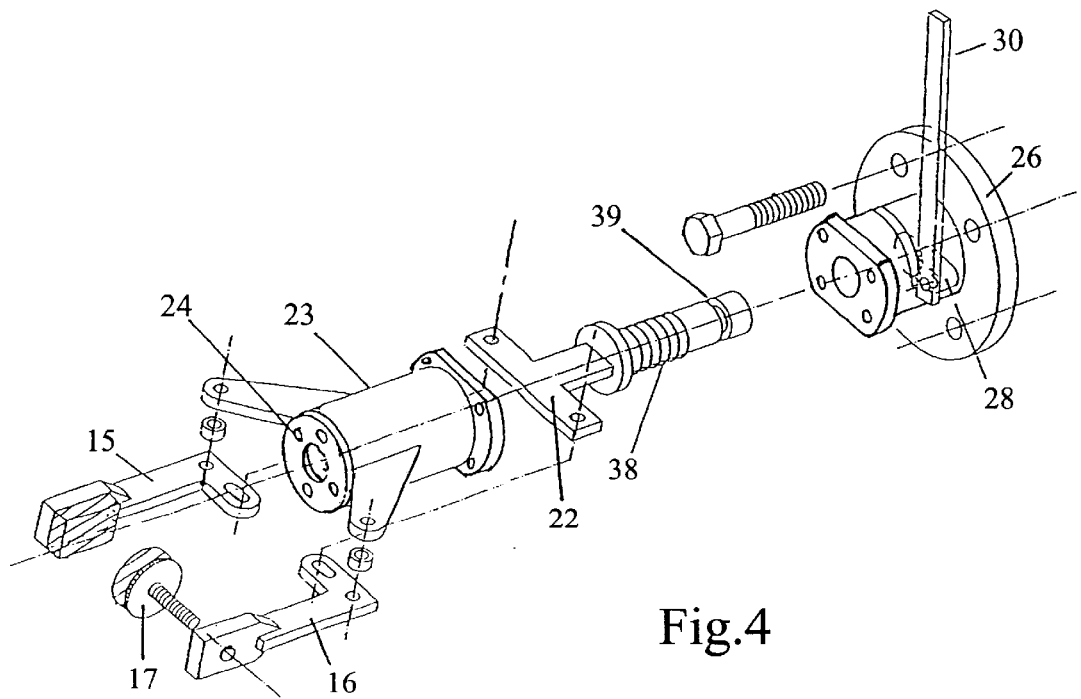

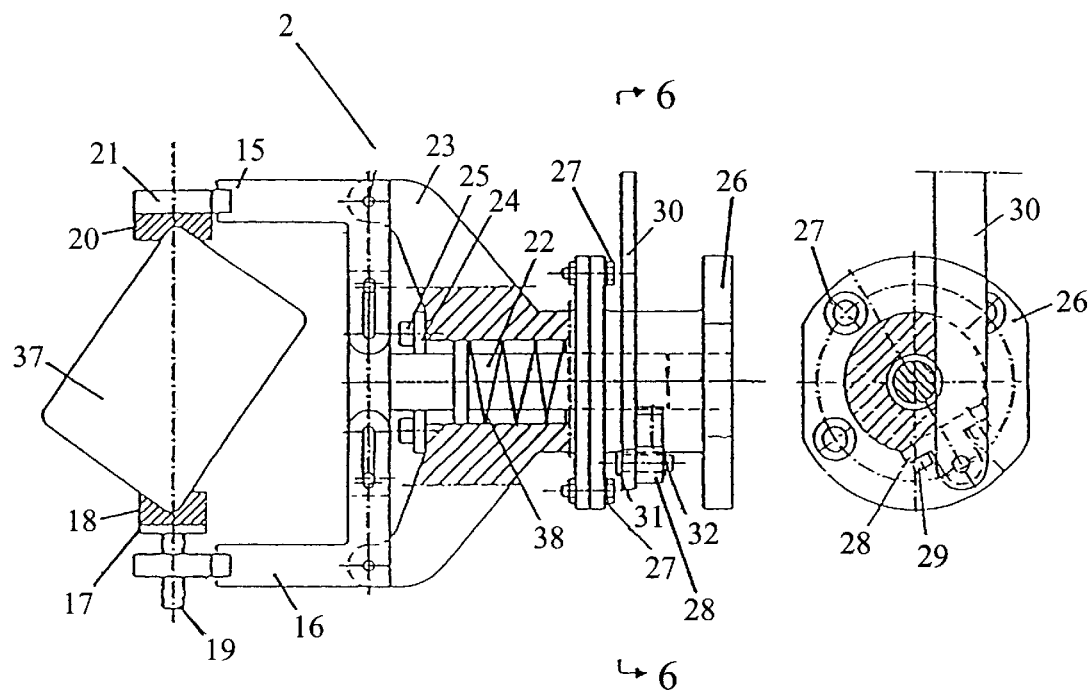
Fig.5
Fig.6
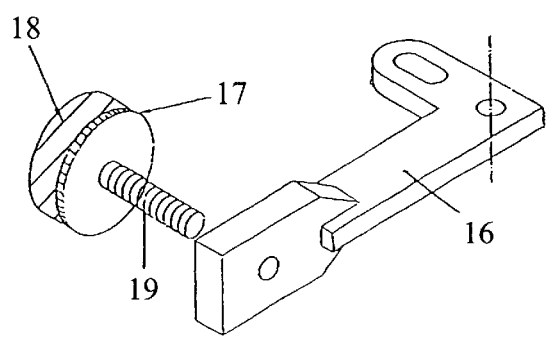
Fig.7
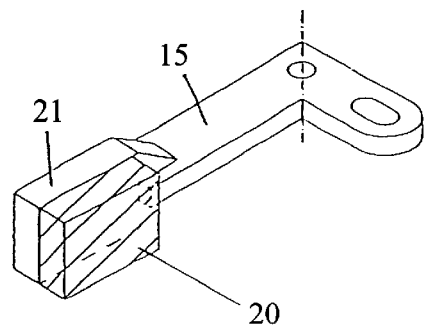
Fig.8

IMPACT DROP TESTER FOR PORTABLE CONSUMER PRODUCTS

FIELD OF THE INVENTION

This invention relates to mechanical-shock fragility testing of portable consumer products such as portable mobile phones, pagers, etc.

BACKGROUND OF THE INVENTION

To assess physical robustness of portable consumer products, manufacturers subject these products to impact and subsequently test their continued function and reliability. Currently, many manufacturers conduct such tests by dropping the product by hand. However, such a drop test is not suitable for controlled repeatability and therefore poses a major problem in verifying test data. To overcome this problem, various drop test devices have been suggested. For example, Japanese Patent No. 1-239465 discloses a mechanical device for elevating a product and dropping it onto a target surface and U.S. Pat. No. 4,910,995 discloses repeat drop tests of a compact disc using a string. An impact testing machine is also disclosed in U.S. Pat. No. 3,412,598, where a test package is propelled at high velocity via a horizontal rail and is disengaged by a quick release mechanism, allowing it to continue its motion towards an impact receiving surface. Although the prior art discloses repeatable drop testing of products there is no disclosure of a generally versatile mechanism which allows for the orientation of the product to be specifically manipulated and controlled for repeat testing.

OBJECT OF INVENTION

It is a primary object of the invention to facilitate drop testing of a portable consumer product at any desired orientation and drop height, to allow assessment of damage to the product when it is subjected to impact at different orientations and from various drop heights.

Other objects, features and advantages of the present invention will become apparent from the detailed description which follows, or may be learned by practice of the invention.

SUMMARY OF INVENTION

In accordance with the invention, there is provided a drop tester including a gripper mechanism for holding a product to be tested, a guide track, a slider block which is mounted to slide along the guide track and advance the mechanism toward a target location and a release device for triggering release of the product from the mechanism to impact at the target location.

Preferably, the gripper mechanism includes gripper arms coupled to the slider block, the gripper arms being rotatable relative to the slider block to enable the orientation of the product to be varied, relative to the target location.

In another aspect, there is provided a gripper mechanism for use in the above drop tester.

BRIEF DESCRIPTION OF ACCOMPANYING DRAWINGS

The accompanying drawings which are incorporated into and constitute a part of the description of the invention, illustrate embodiments of the invention and serve to explain the principles of the invention. It is to be understood, however, that the drawings are designed for purposes of illustration only, and not as a definition of the limits of the invention for which reference should be made to the claims appearing at the end of the description.

FIG. 2 is a sectional side view of a quick release mechanism used in the drop tester;

FIG. 3 is a sectional front view of the quick release mechanism;

FIG. 4 is an exploded isometric view of a gripper mechanism of the drop tester;

FIG. 5 is a plan view of the gripper mechanism, with a piston housing partially sectioned to expose the piston for the purpose of clarity;

FIG. 6 is a sectional view along line 6—6 in FIG. 5;

FIG. 7 is an isometric view of the left gripper;

FIG. 8 is an isometric view of the right gripper;

DESCRIPTION OF A PREFERRED EMBODIMENT OF INVENTION

Figure 1:
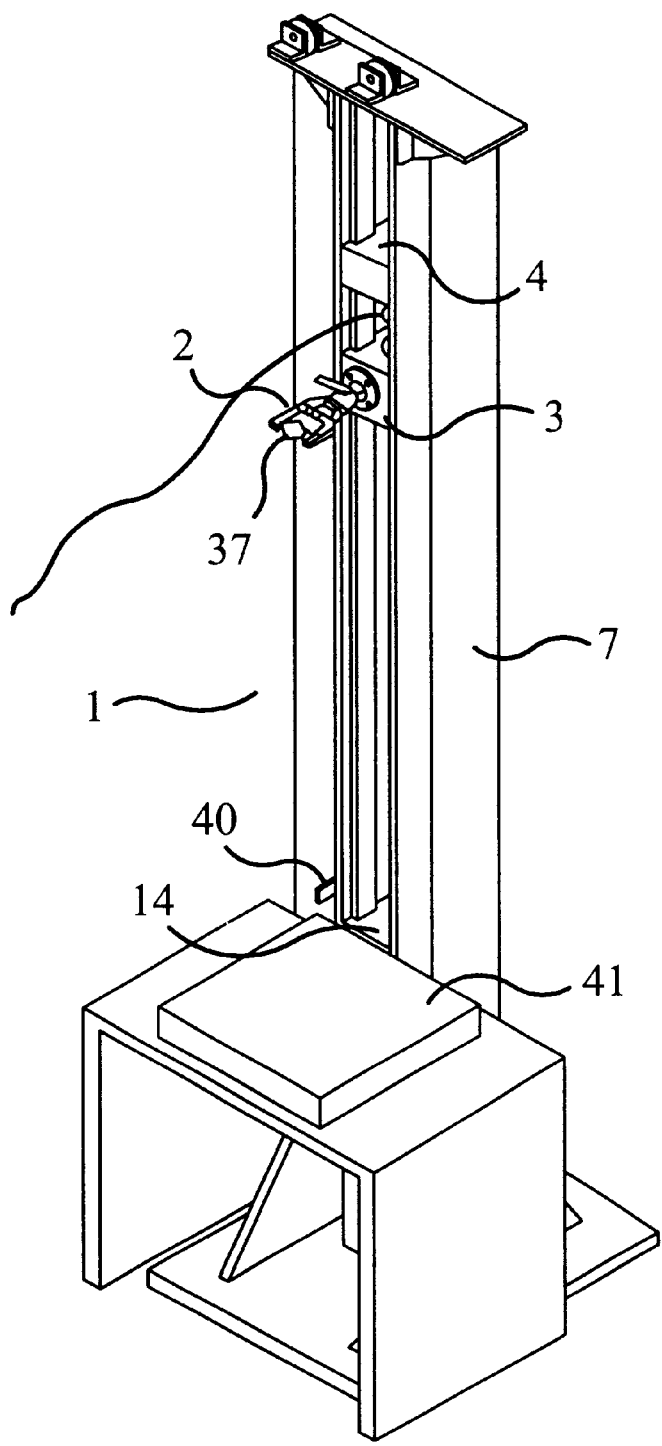
FIG. 1 is an isometric view of an embodiment of a drop tester constructed according to the present invention.

A drop tester 1 is shown in FIG. 1 having a gripper mechanism 2. The gripper mechanism 2 is mounted onto a slider block 3. The slider block 3 is coupled to a hoisting block 4 via a quick release connector 5. This hoisting block 4 can be raised to a desired drop height via the hoisting cable 6. Both the slider block 3 and hoisting block 4 are adapted to slide between a vertical guide track formed by column supports 7. When the coupled hoisting block 4 and slider block 3 are raised to the desired drop height, the slider block 3 can be uncoupled by a quick release connector 5 which is activated by pulling on the release cable 8.

The quick release connector 5 is shown in more detail in FIGS. 2 and 3. A connecting rod 10 is screwed into the slider block 3 and kept in position by a lock nut 9. The connecting rod is in turn attached to a quick-release fixture 11 by a retaining pin 10a resting on a release pin 12. The quick-release fixture 11 is attached to the base of the hoisting block 4 by two screws 13. When the release cable 8 is pulled, the release pin 12 is disengaged from supporting the retaining pin 10a, thus releasing the slider block 3. The slider block 3 then falls freely under gravity, guided by the two vertical column supports 7.

Referring now to FIGS. 4 to 8, the gripper mechanism 2 includes a first gripper arm 15 and a second gripper arm 16 pivotally mounted to a respective flange of a piston housing 23. Inner ends of the gripper arms 15, 16 are coupled to a piston 22 via a pin and slot type engagement such that linear movement of the piston effects pivotal movement of the gripper arms relative to the respective flange from a gripping position to a release position for releasing a product 37. The gripper arm 16 is provided with a gripper jaw 17 with a rubber pad 18 affixed to it. The jaw is adjustable relative to the arm via a screw thread 19. The gripper arm 15 is also formed with a jaw 21, with a rubber pad 20 affixed thereto.

The piston housing 23 is provided with a piston retainer 24 affixed to it via screws 25 to prevent the piston 22 from sliding completely out of the piston housing. The piston housing 23 is connected to a piston housing support 26 by screws 27. A locking bar support 28 is also mounted on the piston housing support 26 via two bolts 29. The locking bar support 28 is mounted to a pin 31 and held on the pin 31 by locking pin 32, to allow for rotation of the locking bar 30 about the pin 31. The locking bar engages with a slot 39 of the piston 22 to releasably hold the piston in a retracted position, against the bias of spring 38. The piston housing support 26 is itself mounted onto the slider block 3.

Figure 9:
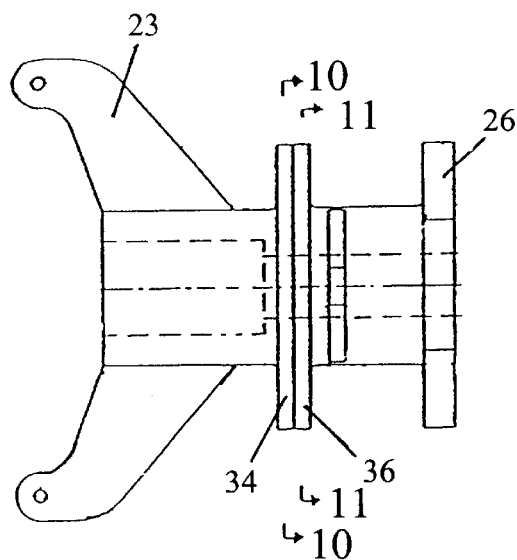
FIG. 9 is a plan view of the piston housing and piston housing support.
Figures 10, 11:
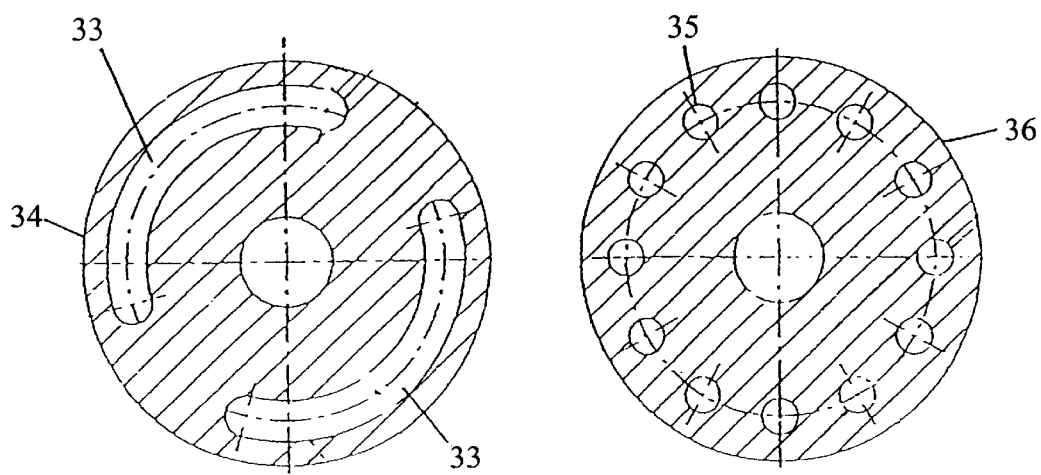
FIG. 10 is a sectional view of the piston housing, taken along line 10—10 in FIG. 9.
FIG. 11 is a sectional view of the piston housing support, taken along line 11—11 in FIG. 9.

FIG. 9 shows the piston housing 23 as being provided with connection flange 34 which connects the housing to the piston housing support 26 via a mating connection flange 36. FIG. 10 shows the connection flange 34 of the piston housing 23, with two curved slots 33 machined into it. This allows the piston housing 23 to rotate to any angle before it is fastened to the mating connection flange 36 of the piston housing support 26. Fastening is effected via bolting through eight of the mounting holes 35 shown in FIG. 11. The ability to rotate the piston housing 23 means that the gripper arms 15, 16 are also rotatable to any angle before the piston housing 23 is fastened to the piston housing support 26, to thereby allow the test product 37 to assume a desired orientation at impact.

With reference to FIG. 5 again, when the gripper jaws 17, 21 are clamped to the product 37, the piston 22 is pushed into the piston housing 23, thus compressing the helical spring 38. To retain the piston 22 within the piston housing 23, the locking bar 30 is pushed into the slot 39 as indicated in FIG. 4. The gripper mechanism 2 is then primed, ready to execute a drop test.

To conduct the test, the coupled slider block 3 and hoisting block 4 are raised to the required drop height, and the release cable 8 connected to the release pin 12 is pulled. This uncouples the slider block 3 with its attached gripper mechanism 2, allowing it to fall freely and slide between the column supports 7. When the slider block descends to the level of a stationary release bar 40, located close to the target impact location/surface 41, contact between the release bar 40 and the locking bar 30 pushes the latter into an unlocked position. This disengages the spring-loaded piston 22, which fires forwardly to rotate the grippers 15, 16 and release the product 37. The product 37 then continues its motion unrestrained for a momentary period before it strikes the target impact surface 41 at the orientation with which it was gripped prior to release. The motion of the slider block 3 is arrested by the shock absorber 14 shown in FIG. 1.

As can be appreciated from the above, many modifications and variations may be made to the drop tester without departing from the spirit and scope of the invention, as described. For example, the slider block and hoisting block may be connected via any suitable means such as electromagnetic coupling, the hoisting block itself may be elevated mechanically such as by a motor and the locking bar and release lever may be replaced with any other appropriate release device suitable for releasing the gripper arms at a predetermined location. The specific form of the gripper arms may also be modified, as desired.

What is claimed is:

1. A drop tester comprising:
a gripper mechanism for holding a product to be tested;
a guide track;
a slider block which is mounted to slide along the guide track and advance the gripper mechanism and the product toward a target location; and
a release device for triggering a release of the product from the gripper mechanism to induce an impact at the target location, the gripper mechanism including gripper arms coupled to the slider block, the gripper arms being rotatable relative to the slider block to enable an orientation of the product to be varied relative to the target location.

2. A drop tester as claimed in claim 1, further comprising a hoisting block positionable at a predetermined location along the guide track, wherein the slider block is releasably coupled to the hoisting block.

3. A drop tester as claimed in claim 2, further comprising:
a connecting rod; and
a retaining pin, wherein the hoisting block and the slider block are coupled by the connecting rod which is releasably held in the hoisting block by the retaining pin which is arranged to be retracted to release the slider block from the hoisting block.

4. A drop tester comprising:
a gripper mechanism for holding a product to be tested;
a guide track;
a slider block which is mounted to slide along the guide track and advance the gripper mechanism toward a target location;
a release device for triggering a release of the product from the gripper mechanism to induce an impact at the target location; and
gripper arms arranged to rotate relative to a support coupling the gripper arms to a slider block of the drop tester.

5. A gripper mechanism as claimed in claim 4, wherein the gripper arms are pivotally mounted on a housing and coupled to a piston provided within the housing, the gripper arms pivoting between a gripping position and a release position upon an advancement of the piston through the housing.

6. A gripper mechanism as claimed in claim 5, the housing including a spring therewithin and the piston being held against a spring bias of the spring in a retracted condition when the arms are in a gripping position.

7. A gripper mechanism as claimed in claim 6, the gripper mechanism further including a lock to hold the piston in the retracted condition.

8. A gripper mechanism as claimed in claim 7, the lock further including a pivotal arm mounted relative to the housing; and
a slot, wherein the pivotal arm is adapted to releasably engage the slot in the piston.

9. A gripper mechanism as claimed in claim 5, wherein the housing is mounted to a support and is adapted to rotate relative to the support to effect the rotation of the gripper arms, wherein the housing and support are provided with respective connection flanges, a first one of the flanges having arcuate slots and a second flange having mounting holes for receipt of fastening bolts arranged to pass therethrough to clamp the first and the second flanges together, once the housing is rotated to a desired position.

10. A drop tester comprising:
a gripper mechanism for holding a product to be tested;
a guide track;
a slider block which is mounted to slide along the guide track and advance the gripper mechanism toward a target location;
a release device for triggering a release of the product from the gripper mechanism to induce an impact at the target location, the gripper mechanism including gripper arms coupled to the slider block, the gripper arms being rotatable relative to the slider block to enable an orientation of the product to be varied relative to the target location;

a housing; and a piston provided within the housing, the gripper arms being pivotally mounted to the housing and coupled to the piston provided within the housing, the arms pivoting between a gripping position and a release position upon an advancement of the piston through the housing.

11. A drop tester as claimed in claim 10, the housing including:

a spring within the housing, the piston being held against a spring bias of the spring in a retracted condition, when the arms are in the gripping position.

12. A drop tester as claimed in claim 10, the gripper mechanism including a lock to hold the piston in the retracted condition, the lock being released by the release device.

13. A drop tester as claimed in claim 12, wherein the lock further includes a pivotal arm mounted relative to the housing and adapted to releasably engage a slot in the piston.

14. A drop tester as claimed in claim 10, further comprising a support provided on the slider block, wherein the housing is mounted to the support provided on the slider block and is adapted to rotate relative to the support to effect a rotation of the gripper arms.

15. A drop tester as claimed in claim 14, wherein the housing and support are provided with respective connection flanges, a first one of the flanges having arcuate slots and a second of the flanges having mounting holes for receipt of fastening bolts arranged to pass therethrough, to clamp the connection flanges together once the housing is rotated to a desired position.

* * * * *